(12) United States Patent
Zhao

(10) Patent No.: US 8,992,611 B2
(45) Date of Patent: Mar. 31, 2015

(54) MICROINCISION LENS

(75) Inventor: Huawei Zhao, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 555 days.

(21) Appl. No.: 12/875,850

(22) Filed: Sep. 3, 2010

(65) Prior Publication Data

US 2012/0059464 A1 Mar. 8, 2012

(51) Int. Cl.
*A61F 2/16* (2006.01)

(52) U.S. Cl.
CPC .............. *A61F 2/1654* (2013.01); *A61F 2/1656* (2013.01)
USPC ........................................................ 623/6.28

(58) Field of Classification Search
USPC .................... 623/5.16, 6.18–6.21, 6.23–6.25, 623/6.27–6.28, 6.3, 6.43
See application file for complete search history.

(56) References Cited

U.S. PATENT DOCUMENTS

| | | | | |
|---|---|---|---|---|
| 4,666,446 A * | 5/1987 | Koziol et al. | ................ | 623/6.33 |
| 4,759,761 A * | 7/1988 | Portnoy | ....................... | 623/6.11 |
| 4,778,462 A * | 10/1988 | Grendahl | ..................... | 623/6.27 |
| 4,898,461 A * | 2/1990 | Portney | .................... | 351/159.42 |
| 5,017,000 A | 5/1991 | Cohen | | |
| 5,120,120 A * | 6/1992 | Cohen | ...................... | 351/159.49 |
| 5,507,806 A * | 4/1996 | Blake | ............................ | 623/6.33 |
| 5,609,630 A * | 3/1997 | Crozafon | .................... | 623/6.43 |
| 5,619,289 A * | 4/1997 | Seidner et al. | ........... | 351/159.47 |
| 6,726,323 B2 * | 4/2004 | Miyamura et al. | ....... | 351/159.14 |
| 7,021,760 B2 * | 4/2006 | Newman | .................. | 351/159.03 |
| 2003/0065387 A1 * | 4/2003 | Callahan et al. | ............. | 623/6.25 |
| 2009/0270984 A1 * | 10/2009 | Sanger et al. | ................ | 623/6.37 |
| 2010/0066973 A1 | 3/2010 | Portney | | |

FOREIGN PATENT DOCUMENTS

| | | | | |
|---|---|---|---|---|
| EP | 2033596 A1 | 3/2009 | | |
| WO | WO2004107020 A2 | 12/2004 | | |
| WO | WO 2007145082 A1 * | 12/2007 | ................ | A61F 2/16 |
| WO | WO 2012031211 A1 * | 3/2012 | ................ | A61F 2/16 |

OTHER PUBLICATIONS

"Optics for Kids", Synopsys, Inc. article located online Oct. 5, 2012 at web address http://www.opticalres.com/optics_for_kids/kidoptx_p2.html.*

* cited by examiner

*Primary Examiner* — Paul Prebilic
(74) *Attorney, Agent, or Firm* — Abbott Medical Optics Inc.

(57) ABSTRACT

A foldable lens comprises an outer refractive surface portion comprising a first plurality of convexly curved refractive profile regions having positive optical power to converge light energy with refraction toward a focus on the retina. The convexly curved refractive profile regions of the outer region may correspond to at least about a quarter of the refractive power of the lens, such that the lens thickness is decreased substantially and the folded lens can fit through a small incision. The outer refractive surface portion focuses light with refraction, in focus images viewed through the outer portion of the lens can appear sharp to the patient. The outer refractive surface portion also comprises a second plurality of concavely curved refractive profile regions having negative optical power disposed between the first plurality, so as to diverge the light energy substantially away from the focus on the retina, such that visual artifacts are inhibited.

16 Claims, 6 Drawing Sheets

MICROINCISION LENS

BACKGROUND OF THE INVENTION

Embodiments of the present invention relate to vision correction, and in particular to ophthalmic lenses such as contact lenses, spectacles, intraocular lens, or corneal onlays, for example.

People like to see, and the eye is critical for vision. Vision can include distance vision for viewing distant objects and near vision for viewing near objects. Examples of distant objects can include stars and street signs. Examples of near objects can include printed text of a book or a computer screen, for example. Useful vision can also include central vision and peripheral vision. Central vision can be important for viewing objects with high visual acuity, such as reading signs at night. Peripheral vision can be important for detecting peripheral objects, such as speeding and potentially harmful object coming into the field of view such as a speeding car or a projectile, and the human eye has a wide field of view to sense such objects.

In at least some instances the vision of the eye may be less than ideal and it can be helpful to provide a person with a lens so as to improve vision. For example, spectacles, contact lenses and intraocular lenses can be used to improve vision.

In at least some instances, a component of the eye can become degraded such that replacement of the component can be helpful. For example, the natural crystalline lens of the eye can degrade and may form a cataract such that a patient may receive an intraocular lens (hereinafter "IOL") to replace the degraded natural crystalline lens.

Although prior IOLs can be used to replace the degraded crystalline lens and improve vision, at least some prior IOLs can be less than ideal in at least some instances. For example, with IOL surgery, a small incision can be made in the eye near the limbus at the periphery of the cornea. The lens inserted through the incision can cause minor distortion of the cornea that may affect patient vision in some instances. For example, the incision near the edge of the cornea may change the shape of the cornea such that the patient vision with the IOL can be less than ideal in at least some instance. Also, the eye may have chromatic aberration and monochromatic aberration prior to incision, and at least some prior foldable IOLs may not be not well suited to correct chromatic aberration or monochromatic aberration in at least some instances.

Although diffractive lenses and Fresnel lenses have been used with prior IOLs, these lenses can produce patient vision that is less than ideal in at least some instances. For example, although diffractive optics can be designed to work well at a specified monochromatic design wavelength, people like to see in color and in at least some instances diffractive optics can scatter light and produce patient perceptible color artifacts at wavelengths away from the design wavelength. Also, diffractive optics can scatter oblique light for peripheral viewing such that peripheral vision with diffractive optics can be degraded more than would be ideal in at least some instances. With Fresnel lenses, images can be degraded and light scatter associated with steps of the Fresnel lens can degrade vision at least partially in at least some instances. Also, oblique light for peripheral viewing can scatter and degrade peripheral vision with Fresnel lenses in at least some instances. Consequently, prior efforts IOLs having diffractive optics or Fresnel lenses have provided less than ideal vision in at least some instances.

In view of the above, it would be helpful to provide improved lenses to correct vision. Ideally such lenses would overcome one or more of the above deficiencies of the prior lenses. For example, a lens that is foldable to a size that fits through a small incision to correct vision with decreased tissue distortion and improved correction of aberrations and improved peripheral vision when positioned would be helpful.

BRIEF SUMMARY OF THE INVENTION

Embodiments of the present invention provide improved lenses that can be inserted through a small incision and unfolded so as to correct at least some aberrations of the eye. Although specific reference is made to intraocular lenses, embodiments as described herein can be used with many forms of vision correction such as contact lenses, spectacles, and implantable lenses such as intraocular lenses corneal inlays. The foldable lens may comprise a first side having a first optical surface disposed thereon, which first optical surface may be have an inner optical surface portion and an outer refractive surface portion. The outer refractive surface portion may comprise a first plurality of convexly curved refractive profile regions having positive optical power to converge light energy with refraction toward a focus on the retina, such that the overall thickness of the lens can be decreased substantially. The convexly curved refractive profile regions of the outer portion may correspond to at least about a quarter of the refractive power of the lens, for example about half of the power, such that the central lens thickness can be decreased substantially and the folded lens can fit through the small incision. As the outer refractive surface portion can focus light with refraction, in focus images viewed through the outer portion of the lens can appear sharp to the patient for both central and peripheral vision. The outer refractive surface portion may comprise a second plurality of concavely curved refractive profile regions having negative optical power disposed between the first plurality so as to diverge the light energy substantially away from the focus on the retina, such that visual artifacts such as ghost images, halos and diploplia can be inhibited substantially for both central and peripheral vision. The outer refractive surface portion of the foldable lens can be disposed on a first side of the lens and combined with monochromatic aberration correction and chromatic aberration correction, for example, such that the patient can have very good vision through the unfolded lens.

In a first aspect, embodiments of the present invention provide a foldable lens for insertion into an eye of a patient through an incision, in which the eye has a retina. The foldable lens comprises an optically transparent foldable material having a first side disposed opposite a second side. The first side comprises an inner optical surface portion and an outer refractive surface portion. The outer refractive surface portion comprises a first plurality of convexly curved refractive profile regions to converge light energy with refraction toward a focus on the retina. The outer refractive surface portion also comprises a second plurality of concavely curved refractive profile regions disposed between the first plurality so as to diverge the light energy away from the focus on the retina.

In many embodiments, the first plurality of convexly curved refractive profile regions comprises first annular regions, and the second plurality of concavely curved refractive profile regions comprises second annular regions disposed between the first annular regions.

In many embodiments, the second side comprises a second optical surface coupled to the inner optical surface portion and the outer refractive surface portion. The second optical surface may comprise a convex refractive surface profile having a positive optical power optically coupled to the inner optical surface portion and the outer refractive surface portion, and each of the concavely curved refractive profile regions may comprise a negative optical power stronger than the positive optical power of the convex refractive surface profile to diverge the light energy away from the focus when placed in the eye. Each of the convexly curved refractive profile regions may comprise a positive optical power coupled to the positive optical power of the convex refractive surface so as to direct the light energy toward the focus, and the negative optical power of each concavely curved refractive profile region may be stronger than the positive optical power of said each of the convexly curved refractive profile regions.

In many embodiments, the convex refractive surface profile of the second side comprises a diffractive profile disposed thereon. The diffractive profile may comprise one or more of a substantially monofocal diffractive profile having positive optical power to correct chromatic aberration of the eye or a multifocal diffractive profile having positive optical power to correct chromatic aberration and increase a depth of field of the focus so as to mitigate presbyopia, for example.

In many embodiments, the convex refractive surface profile comprises one or more of a spherical surface, a toric surface, an aspheric surface, a conic constant, a fourth order spherical aberration correction or a sixth order spherical aberration correction.

In many embodiments, the first side comprises an anterior side and the second side comprises a posterior side when positioned in the eye, although the first side may comprise the posterior side and the second side may comprise the anterior side.

In many embodiments, the second optical surface comprises a diffractive surface profile having a positive optical power, and the diffractive surface profile is optically coupled to the inner optical surface portion and the outer refractive surface portion. Each of the concavely curved refractive profile region may comprise a negative optical power stronger than the positive optical power of the diffractive surface profile so as to diverge the light energy away from the focus when placed in the eye.

In many embodiments, the inner optical surface portion comprises a convex refractive surface profile. Alternatively or in combination, the inner optical surface portion may comprise a diffractive surface profile.

In many embodiments, the first side comprises one or more of a spherical surface, a toric surface, an aspheric surface, a conic constant correction, a fourth order spherical aberration correction or a sixth order spherical aberration correction to correct monochromatic aberrations of the eye, for example of the spherical aberration of the cornea.

In many embodiments, the second optical surface comprises one or more of a spherical surface, a toric surface, an aspheric surface, a conic constant correction, a fourth order spherical aberration correction or a sixth order spherical aberration correction to correct monochromatic aberrations of the eye, for example of the monochromatic aberration of the cornea. For example, the surfaces of each of the first side and the second side may comprise a conic constant correction, a fourth order spherical aberration correction and a sixth order spherical aberration correction to correct monochromatic aberrations of the eye when the unfolded lens is positioned in the eye.

In many embodiments, the foldable lens comprising an intraocular lens (IOL) having at least two haptics affixed to the lens.

In many embodiments, the optically transparent foldable material comprises one or more of a hydrogel material, a silicone material or a soft acrylic material.

In many embodiments, the foldable lens comprises a foldable IOL having an optically used portion having a maximum distance across of at least about 5 mm and an optical power of at least about +5 D, for example at least about +15 D, and a center thickness of the optically used portion comprises no more than about 0.7 mm.

In another aspect, embodiments of the present invention provide a method of treating an eye of a patient having a retina. An IOL is inserted having a folded elongate narrow profile configuration through an incision of the eye. The IOL is positioned to correct vision with an expanded wide profile configuration such that an inner optical surface portion of the IOL refracts light toward a focus on the retina and an outer refractive surface portion of the IOL refracts light away from a focus on the retina.

In many embodiments, the outer portion comprises a first plurality of convexly curved refractive profile regions having positive optical power, and the second plurality of concavely curved refractive profile regions having negative optical power and wherein each of the concavely curved refractive profile regions has sufficient optical power refract light away from the focus on the retina such that patient perceptible artifacts are substantially inhibited when the eye views a light source at night.

In many embodiments, the incision comprises a length of no more than about 2 mm across and wherein the elongate narrow profile configuration has a maximum distance across of no more than about 2 mm when the IOL has an optical power of at least about +5 D, for example at least about +15 D. The IOL may comprise an optically used portion having a maximum distance across of at least about 5 mm, and a central thickness of the optically used portion may comprise no more than about 0.7 mm.

In many embodiments, the inner optical surface portion and the outer refractive surface portion are located on a first side of the IOL opposite a second side of the IOL, and the first side comprises an anterior side and the second side comprises a posterior side when positioned in the eye. Alternatively, and the second side may comprise the anterior side and the first side may comprises the posterior side when positioned in the eye.

DETAILED DESCRIPTION OF THE INVENTION

The lenses as described herein can be used with many forms of vision correction, and can be used in many applications where a thin lens is well suited such as placement in or on the eye. The lenses can be well suited for vision correction with many ophthalmic uses of lenses such as contact lenses, spectacles, intraocular lenses and corneal inlays.

As used herein a convexly curved surface of a lens encompasses a surface having positive optical power that converges light rays passing through the surface.

As used herein a concavely curved surface of a lens encompasses a surface having negative optical power that diverges light rays passing through the surface.

The curved surfaces a described herein may comprise one or more of a spherical curved surface, an aspheric curved surface, a toric surface, a cylindrical surface, an elliptical surface having a conic constant, a parabolic surface, or a surface corresponding to a polynomial expansion such as a Taylor Series, a Fourier Series or Zernike polynomials.

Figure 1:
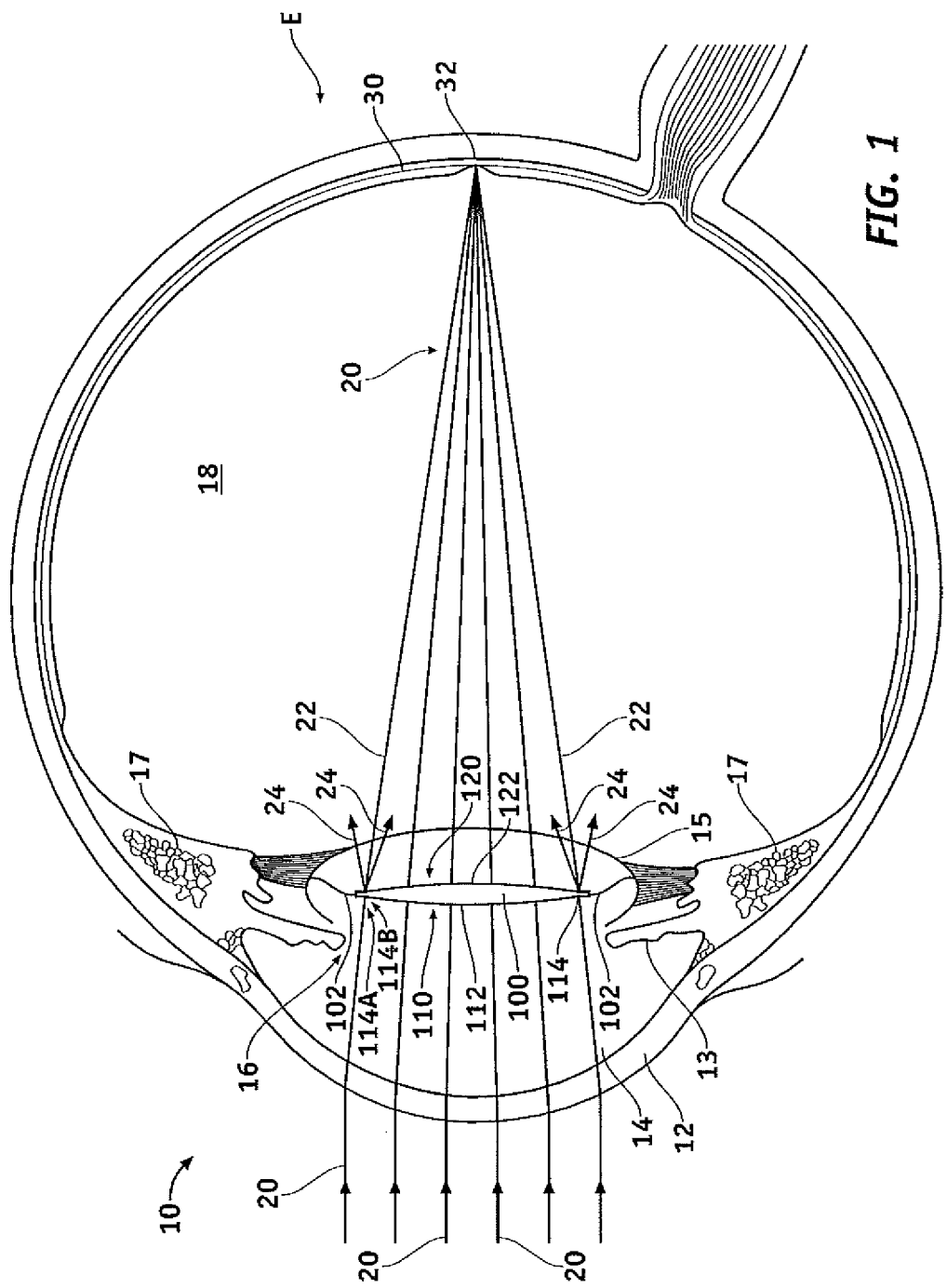
FIG. 1 is a side cross-sectional view of an eye with a foldable intraocular lens, in accordance with embodiments of the present invention.

FIG. 1 shows a side cross-sectional view of an eye E. The eye E has optical components 10 to focus light rays 20 on retina 30, for example on a fovea 32 of retina 30. The optical components 10 comprise a cornea 12, an aqueous humor 14, a lens 16, and a vitreous humor 18. The eye comprises an iris 13 that can define a pupil of the eye E, and the iris 13 can be disposed between the cornea 12 and lens 16 so as to limit the size of the optically used portions of the cornea and lens. The cornea may have about 40 Diopters (hereinafter "D") of optical power, for example about 43 D in at least some patients, such that light rays 20 passing through the cornea 12 can converge at least partially toward the lens 16. The lens 16 provides additional optical power and further converges light rays 20 to a focus on the retina 20. The distance from the cornea 12 to the retina 30 can vary among individuals and can be about 24 mm, for example.

In at least some instances it can be helpful replace the natural crystalline lens of the eye with an intraocular lens. In a patient who has undergone cataract surgery, the lens 16 may comprise foldable intraocular lens 100. The foldable intraocular lens can be sized to fit the eye with an appropriate refractive power so as to correct vision of the patient. The foldable intraocular lens 100 may comprise one or more optical surfaces to correct aberrations of the eye such as spherical aberration.

The foldable intraocular lens 100 has an optically used portion that corresponds to at least a portion of cornea 12 at the front of eye E and is generally centered about the optical axis of eye E. The foldable intraocular lens 100 can be held in place in the eye with at least two haptics 102, for example.

The foldable lens 100 has a first side 110 and a second side 120. Each side of lens 100, including the anterior (front) surface and posterior (back) surface, generally has at least a refractive profile disposed thereon to correct vision of the patient. For example, the first side 110 may comprise an anterior side and the second side 120 may comprise a posterior side when placed in the eye.

The first side 110 may comprise an inner optical surface portion 112 and an outer portion 114. The inner optical surface portion 112 may comprise a central portion of the anterior surface of the lens, for example, and may have a substantially continuous refractive surface to correct vision of the patient.

The foldable intraocular lens can be placed in front of the posterior capsule 15 of the lens 16. The foldable intraocular lens 100 can be folded with the at least two haptics 102 and passed through an incision of no more than about 2.1 mm diameter, for example, such that post surgical distortion of cornea 12 can be decreased substantially when the patient receives the aberration correcting foldable intraocular lens 100. The foldable IOL can be inserted having a folded elongate narrow profile configuration through the incision of the eye. The IOL is positioned to correct vision with an expanded wide profile configuration such that an inner optical surface portion 112 of the IOL refracts light toward a focus on the retina. An outer refractive surface portion 114 of the IOL refracts light toward the focus on the retina with a first plurality of convexly curved refractive profile regions and away from the focus on the retina with a second plurality of concavely curved refractive surface profile regions.

The outer portion 114 may can be disposed outside the inner optical surface portion 112 so as to provide a narrow profile lens foldable lens with substantial aberration correction and inhibited visual artifacts. The outer portion 114 can have a first plurality of convexly curved refractive surface profile regions 114A and a second plurality of concavely curved refractive profile regions 114B. The first plurality of convexly curved refractive surface profile regions 114A can refract outer light rays 22 so as to converge toward a focus on retina 30, for example toward a focus on fovea 32. The second plurality of concavely curved refractive surface profile regions 114B can diverge outer light rays 24 away from focus on the retina so as to inhibit formation of visual artifacts such as ghost images, halos, and diploplia when the eye views objects with dim illumination such as objects at night, for example, such as point sources of light. The second plurality of concavely curved refractive surface profile regions 114B may comprise substantial optical power, for example −10 D or more, such that divergent outer light rays 24 are spread uniformly over a large region of the retina so to that visual artifacts are inhibited. The divergent outer light rays may comprise an amount of light energy with in a range from about 5% to about 50% of the light energy passing through the outer portion 114, for example within a range from about 7% to about 20% of the light energy passing through the outer portion 114.

The second side 120 of foldable lens 100 can be configured in many ways to provide vision for the patient. For example, second side 120 may comprise a convex refractive surface with spherical aberration correction. The second side 120 may comprise a diffractive optical patter disposed on the refractive surface, for example so as to provide one or more of chromatic aberration correction or multifocal correction to increase a depth of field of the eye.

In a young, healthy eye contraction and relaxation of ciliary muscles 17 surrounding the natural lens 16 contribute to accommodation of the eye, the process by which the eye increases optical power to maintain focus on objects as they move closer. As a person ages, the degree of accommodation decreases and presbyopia, the diminished ability to focus on near objects, often results. A patient may therefore need corrective optics having two optical powers, one for near vision and one for far vision, which can be provided by multifocal diffractive IOL disposed on one the sides of lens 100, for example.

Figure 2A:
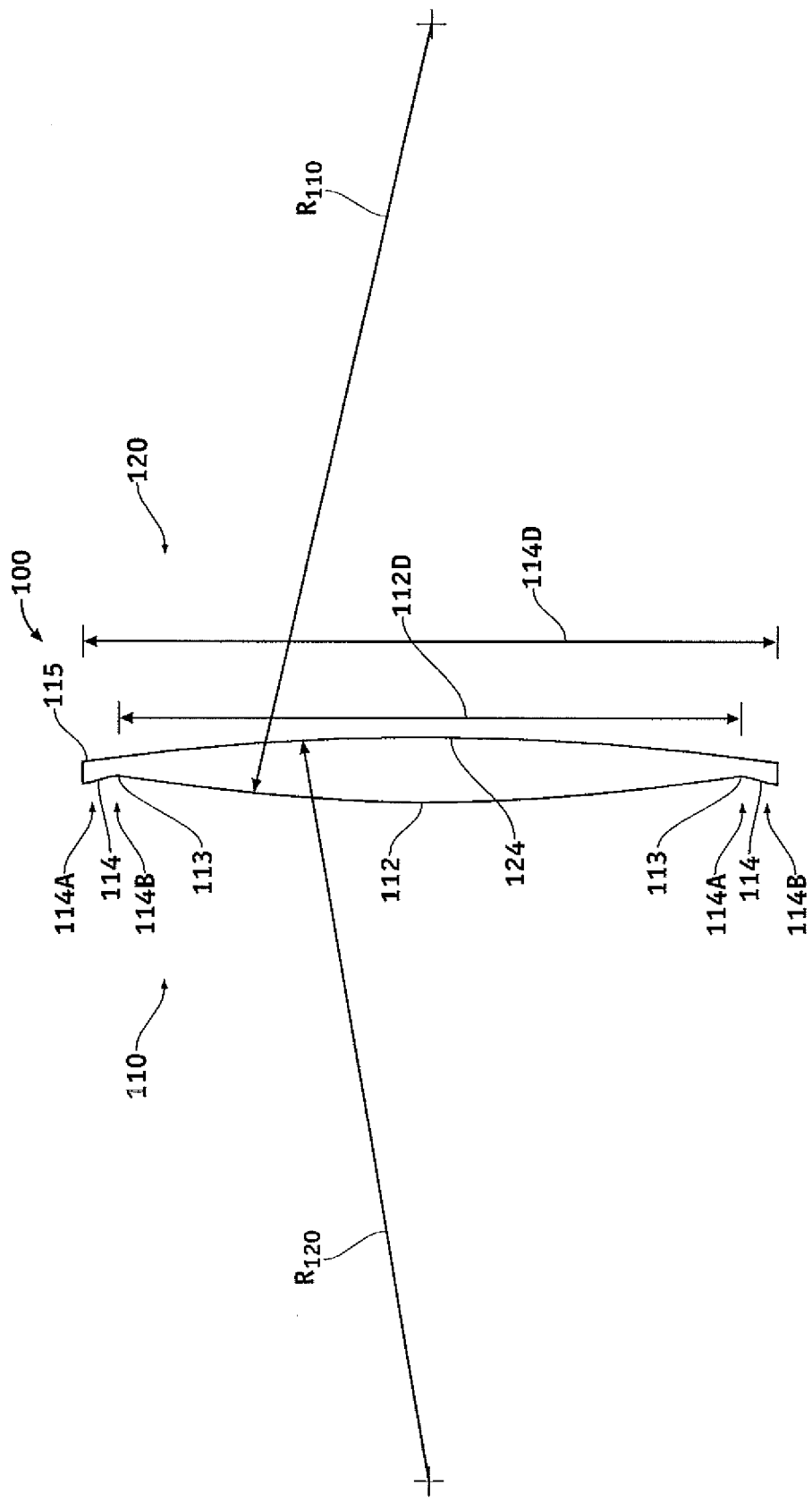
FIG. 2A is a side cross-sectional view of a foldable ophthalmic lens as in FIG. 1.

FIG. 2A is a side cross-sectional view of a foldable ophthalmic lens as in FIG. 1. The first side 110 may have a corresponding first radius of curvature R110, and the second side 120 may have an optical surface 124 corresponding second radius of curvature R120. The inner optical surface portion 112 may extend to a boundary 113 and may comprise a substantially circular disc shape region, for example, having the radius of curvature 110. The outer portion 114 can extend from boundary 113 to an outer boundary 115. The inner optical surface portion may comprise a maximum distance across, for example a diameter 112D, and the outer portion may comprise a maximum distance across, for example a diameter 114D. The outer portion can be sized such that light refracted by outer portion 114 is transmitted through second side 120 and refracted by the second side.

The optically used portion of foldable lens 100 comprising inner portion 112 and outer portion 114 can be sized in many ways. For example, diameter 112D of the inner portion can be within a range from about 4 mm to about 6 mm, for example within a range from about 4.5 mm to about 5.5 mm. The diameter 114D of the outer portion can be within a range from about 4 mm to about 8 mm, for example within a range from about 4.5 mm to about 6.5 mm.

Figure 2B:
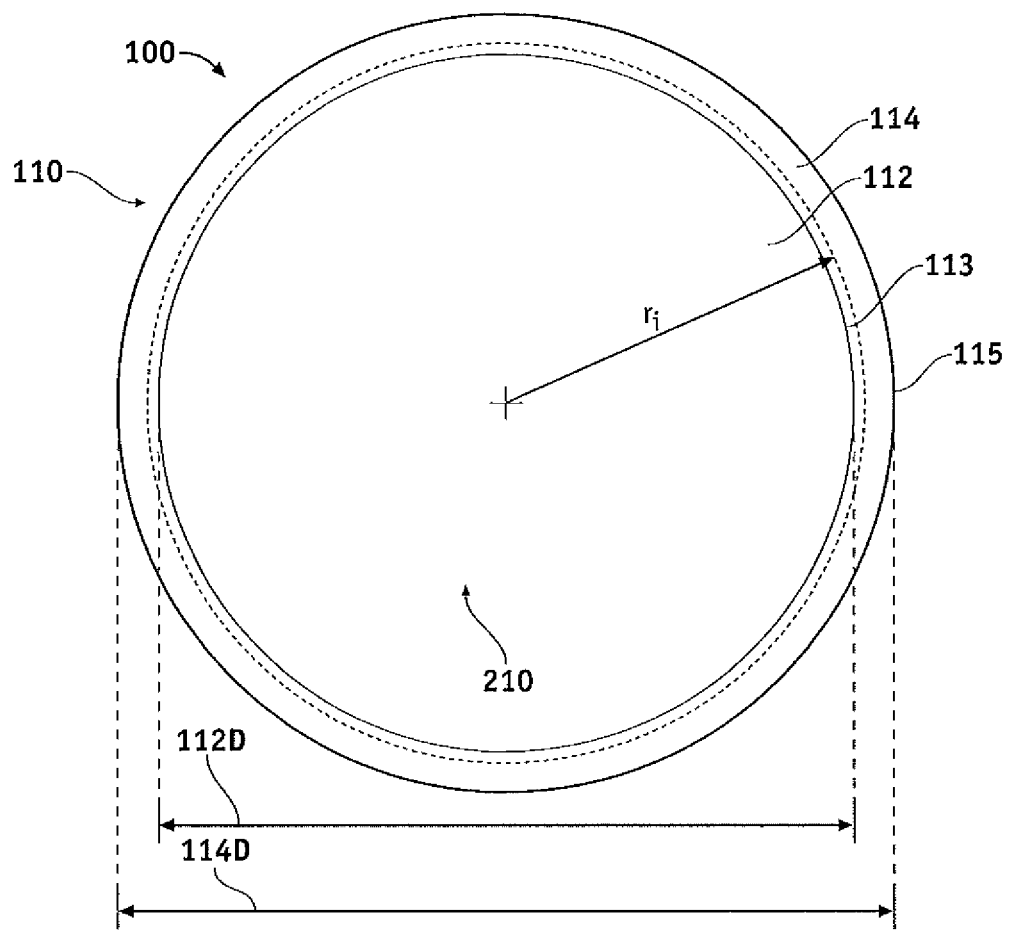
FIG. 2B shows a top view of the foldable lens of FIGS. 1 and 2A.

FIG. 2B is a top view of the foldable lens as in FIG. 2A. The first plurality of convexly curved refractive surface profile regions 114A and the second plurality of concavely curved refractive profile regions 114B can be defined by a plurality of radii ri. The plurality of radii ri may correspond to the first plurality of convexly curved refractive surface profile regions 114A disposed between the second plurality of concavely curved refractive profile regions 114B, and vice versa.

Figure 2C:
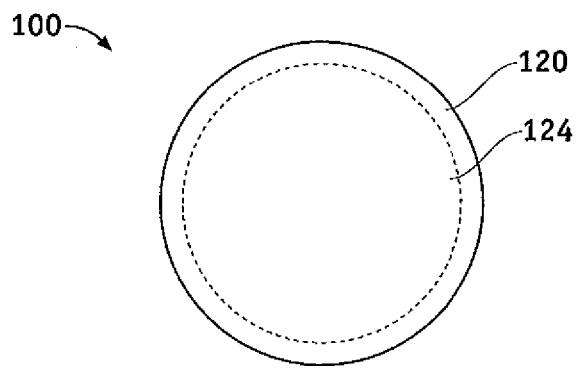
FIG. 2C is a bottom view of the foldable lens of FIGS. 1, 2A and 2B.

FIG. 2C shows a bottom view of the foldable IOL 100. of FIGS. 1, 2A and 2B. The second side 120 may comprise optical surface 124 sized to couple to the inner optical surface portion 112 and the outer portion 114.

Figure 2D:
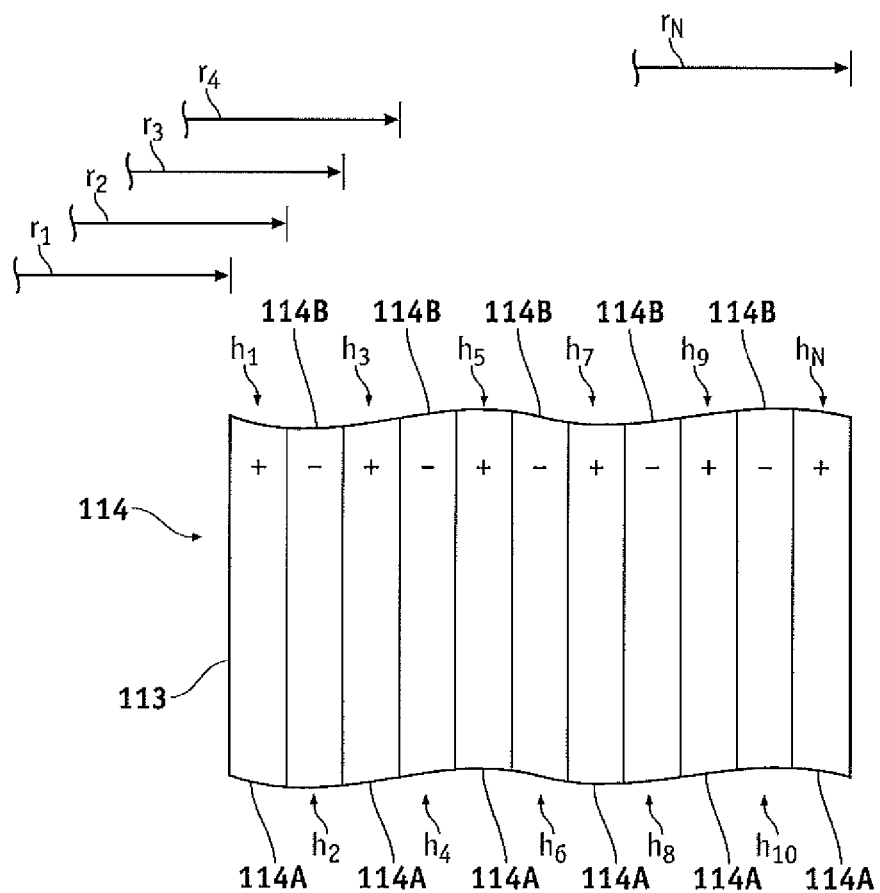
FIG. 2D shows a top view of first plurality of convexly curved refractive profile regions disposed between a second plurality of concavely curved refractive profile regions of an outer portion of the foldable lens, in accordance with embodiments.

FIG. 2D shows a top view of a part of the outer portion of the first side of the lens comprising the first plurality of convexly curved refractive profile regions 114A disposed between a second plurality of concavely curved refractive profile regions 114B of an outer portion of the foldable lens. Each of the regions may correspond to a radial distance from the center of the lens defined the by plurality of radii ri. For example, a first curved profile region h1 may comprise a convexly curved region so as to converge light rays 122 and can be disposed along boundary 113. First annular curved profile region h1 may comprise a first annular distance across extending from r1 to r2. A second curved annular region h2 can extend from r2 to r3 and may comprise a concavely curved annular region so as to diverge light rays 24 away from the focus. A third curved profile region h3 may comprise a convexly curved refractive profile region and can comprise an annular distance extending from r3 to r4. Each of the distances corresponding to values of the plurality of radii can be substantially the same such that the annular distance of each region is approximately equidistant. The outer portion 114 may comprise additional curved profile regions such as h4, h5, h6, h7, h8, h10 . . . hN. The profile regions having an odd subscript may correspond to convexly curved refractive profile regions having positive optical power and the profile regions having negative subscripts may correspond to concavely curved refractive profile regions having negative optical power. The convexly curved regions can be equidistant with a first distance across each convexly curved region, and the concavely curved regions can be equidistant with a second distance across each concavely curved region, for example. The first distance across each of the convexly curved regions can be different than the second distance across each of the concavely curved regions, such that an amount convergent light from the convexly curved regions can differ from an amount of divergent light energy from the concavely curved regions.

The curved profile regions can be one or more of many shapes such as annular, oval or conical, for example.

Figure 2E:
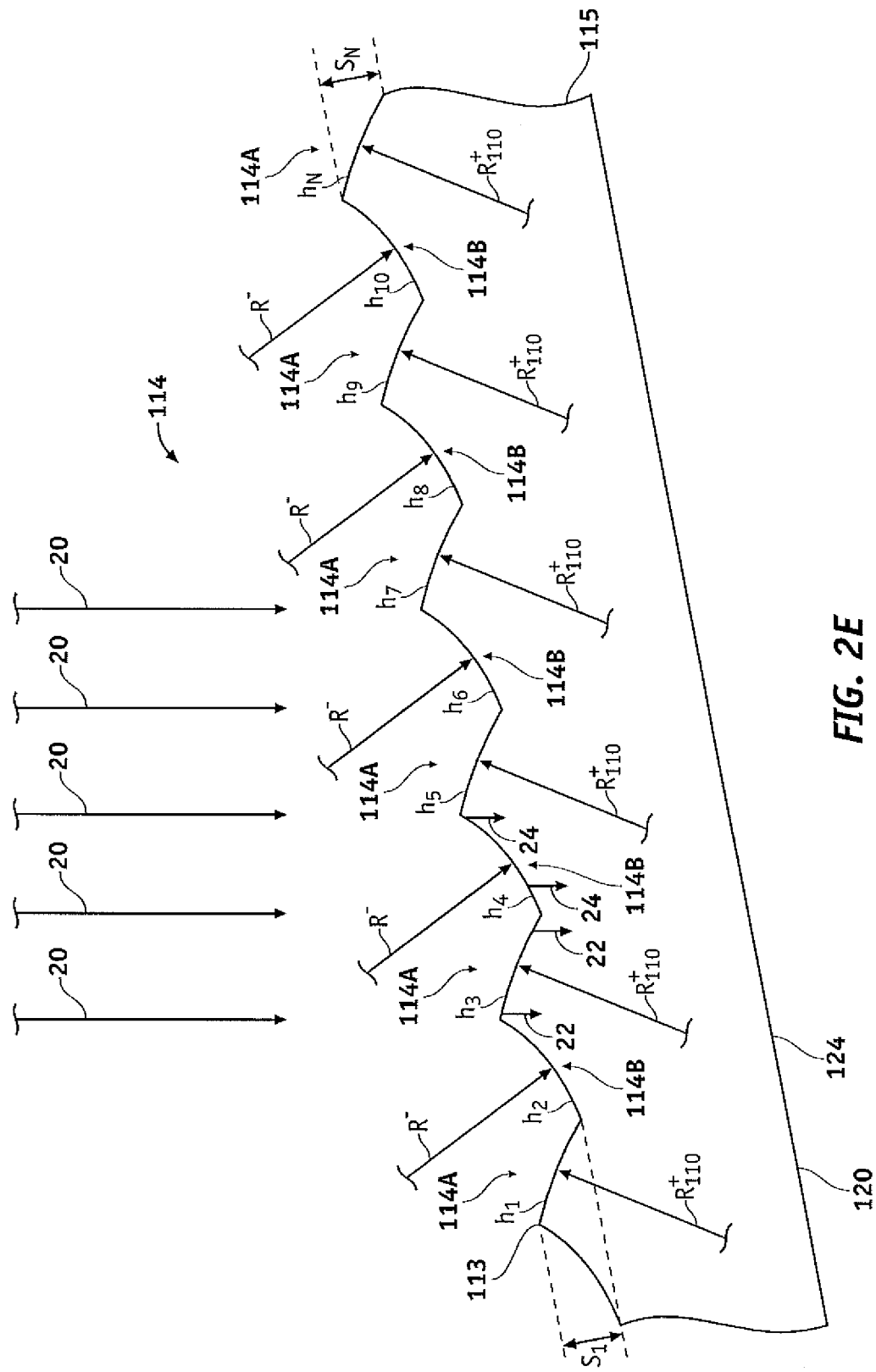
FIG. 2E shows a side cross sectional view the first plurality of convexly curved refractive profile regions disposed between the second plurality of concavely curved refractive profile regions of the outer portion of the foldable lens, in accordance with embodiments.

FIG. 2E shows a side cross sectional view the first plurality of convexly curved refractive profile regions 114A disposed between the second plurality of concavely curved refractive profile regions 114B of the outer portion of the foldable lens. A first curved region h1 comprises positive radius of curvature $R^+110$ that corresponds substantially to radius of curvature $R110$ of the inner optical surface portion of the first side and may equal the radius of curvature 110, so as to converge light rays 22 to the focus on the retina. The outer portion 114 may comprise additional curved profile regions such as h4, h5, h6, h7, h8, h10 . . . hN. A second curved region h2 comprises negative radius of curvature $R^-$ that may correspond to at least about twice the optical power of the radius of curvature $R110$ of the inner optical surface portion of the first side, for example, so as to diverge the light rays 24 substantially from the focus. A third curved region h3 comprises positive radius of curvature $R^+110$ so as to converge light rays 22 to the focus on the retina. A fourth curved region h4 comprises negative radius of curvature $R^-$ to diverge light rays 24 away from the focus on the retina. The additional curved profile regions such as h4, h5, h6, h7, h8, h10 . . . hN may comprises positive radius of curvature $R^+110$ to converge for an odd subscript so as to converge light rays 22 and may comprise the negative radius of curvature $R^-$ for an even subscript so as to diverge light rays 24, for example.

The first curved region h1 comprises a height S1 corresponding the curvature and distance across the region. Each of the curved regions may comprise a height corresponding to the curvature of the region and the distance across the region. For example, the Nth region hN may comprise an Nth height SN. The third curved region h3 may comprise a third height. The second curved region h2 extending between the first curved region and the second curved region may comprise a second height intermediate to the first height and the second height so as to connect smoothly the first curve region with the third curved region.

The plurality of convexly curved surfaces connected with the plurality of concavely curved surfaces located on the outer portion 114 can be effective in reducing substantially aberrations of the eye such as one or more of fourth order spherical aberration, sixth order spherical aberration, coma. The height of each curved region can be at least about 2.4 um, corresponding to an optical path difference from the cornea to the retina of about 4 um, for example. The height of each of the plurality of curved regions can be substantially similar, for example when the distance between the regions decreases with distance. Alternatively or in combination, the heights of the curved regions may increase with increasing distance from the center, for example when the distance across each of the plurality of curved regions comprises a substantially similar radial distance across. As the plurality of convexly curved regions and the plurality of concavely curved regions rely on the refraction of light to correct vision, the height of the plurality of curved regions can have many values substantially independent of the wavelength of light refracted by each of the surfaces.

The optical surface 124 of the second side 120 can be coupled to each of the regions of the first plurality and the second plurality.

The following equations are examples of equations that can be used to determine the profile of one or more of the first side of the lens, the second side of the lens, the inner portion of the lens, or the outer portion of the lens, or combinations thereof.

Thin Lens Equation
Thick Lens Equation
Toric Lens Equations
Conic Constant of Ellipse
Taylor Series
Fourier Series
Zernike Orthogonal Polynomials For example, the outer portion of the lens comprising the plurality of convexly curved regions connected with the plurality of concavely curved regions may comprise a profile corresponding to one or more of the above equations so as to correct aberrations of the eye such as one or more of fourth order spherical aberration, sixth order spherical aberration and coma. The optical path difference of such aberrations may change with at least the third power of the radius, for example, such that the outer portion of the lens having the aberration correction profile can substantially improve vision. While either the first side or the second side, or combinations thereof, may comprise the profile to correct such aberrations, in many embodiments the plurality of convexly curved regions connected with the plurality of concavely curved regions have a profile so as to correct the aberrations of the eye.

EXAMPLE 1

Optical Surface Parameters for the First Side 110 and Second Side 120

Tables 1A to 1E show optical surface parameters of the first side 110 and the second side 120 in accordance with embodiments.

Table 1A shows optical surface parameters of the first side and the second side. The optical power of the lens can be determined with the Thin Lens Equation $$D = (n-1)/R$$

where D is the dioptric power, n is index of refraction and R is the radius of curvature. For an example 20 D biconvex foldable lens 100, the radius of curvature R110 of the first side may comprise about 13.4 mm, and the radius of curvature 120 of the second side may comprise about 13.4 mm, and the center thickness about 0.49 mm. The corresponding radius of curvature of the aqueous humor in contact with the foldable lens can be set to −13.4 mm, for example, in accordance with the aqueous humor liquid of the eye in contact with the lens. Alternatively, the first side may comprise an optical power of about 20 D and the second side may comprise a substantially planar surface having an optical power of about 0 D. The index of refraction of the lens material may comprise, for example, about 1.47 for soft acrylate with a dispersion of about 55. The index of refraction of the aqueous humor and vitreous humor may each comprise about 1.336 with a dispersion of about 50.92. The optical surface may comprise a conic constant within a range from about −1.00 to about −1.04, for example within a range from about −1.01 to about 1.03. The first side comprising the inner optical surface portion and the outer refractive optical surface portion can be oriented toward the anterior and the second side comprising the second optical surface can be oriented toward the posterior.

Table 1B shows dimensions of the curved regions of the outer portion 114 of the lens. The outer portion 114 of the lens may comprise from about 5 to about 20 curved regions, for example about 11 curved regions. For example, the first curved region h1 may comprise a convexly curved region extending radially from about 2.25 mm to about 2.275 mm, for example. The second curved region h2 may comprise a concavely curved region extending from about 2.275 to about 2.3 mm, for example.

TABLE 1B

Radial Sizes of the Regions of the Outer Portion 114 of First Side 110.

| # Zones: | 11 |
|---|---|
| h1 | 2.25 |
| h2 | 2.275 |
| h3 | 2.3 |
| h4 | 2.325 |
| h5 | 2.35 |
| h6 | 2.375 |
| h7 | 2.4 |
| h8 | 2.425 |
| h9 | 2.45 |
| h10 | 2.475 |
| h11 | 2.5 |

Table 1C shows curvatures C1 to C11 for each of the regions h1 to h11. The curvature C can be defined as $$C = 1/R.$$

where R is the radius of curvature of the surface for the each region. The curvature of the convexly curved regions C1, C3, C5, C7, C9 ... CN can be 1/R110, for example, such as about 0.0746 for a 20 D biconvex lens. The curvature of the concavely curved regions can be proportional to the curvature of the convexly curved regions and can be from about 1.5 to about 5 times the curvature of the convexly curved regions and with opposite sign so as to diverge light from the focus of the retina. For example, the curvature of the concavely curved regions C3, C5, C7, C9 ... CN can be −3/R110, so as to have about three times the curvature with three times the optical power and opposite the converging portion. For example, the concavely curved regions can have a curvature such as about −0.02129 for the 20 D biconvex lens, for example.

TABLE 1C

Curvatures of the Regions of the Outer Portion 114 of the First Side 110

| C1: | 1/R110 |
|---|---|
| C2: | −3/R110 |

TABLE 1A

Optical Surface Parameters of the Foldable Lens

| OPTICAL COMPONENT | R (mm) | Center Thickness (mm) | Index | Dispersion | Conic Constant | Orientation |
|---|---|---|---|---|---|---|
| Foldable Lens First Side | 13.4 (R110) | 0.56 | 1.470 | 55.00 | −1.00 to −1.04 | ANTERIOR |
| Foldable Lens Second Side | 13.4 (R120) | | 1.47 | 55.00 | | POSTERIOR |
| Aqueous | −13.4 | | 1.336 | 50.92 | −1.00 to −1.04 | |

TABLE 1C-continued

Curvatures of the Regions of the Outer
Portion 114 of the First Side 110

| C3: | 1/R110 |
| C4: | −3/R110 |
| C5: | 1/R110 |
| C6: | −3/R110 |
| C7: | 1/R110 |
| C8: | −3/R110 |
| C9: | 1/R110 |
| C10: | −3/R110 |
| C11: | 1/R110 |

Table 1D shows examples of rotationally symmetric aberrations that can be corrected such as spherical aberration correction. For example, the optical surface of the second side 120 may comprise fourth order spherical aberration correction and sixth order spherical aberration correction. The fourth order spherical aberration correction can be within a range from about −5.0×10-04 to about −15×10-04, for example. The sixth order spherical aberration can be within a range from about 10×10-05 to about 15×10-05, for example. A person of ordinary skill in the art will recognize many values of spherical aberration correction for each of fourth through sixteenth can be used in accordance with the teachings described herein.

TABLE 1D

| Optical Surface of Second Side 120 | Examples of Ranges |
| --- | --- |
| Coeff on r 2: | 0 |
| Coeff on r 4: | −5.0 × 10−04 to about −15 × 10−04 |
| Coeff on r 6: | 10 × 10−05 to about 15 × 10−05 |
| Coeff on r 8: | 0 |
| Coeff on r 10: | 0 |
| Coeff on r 12: | 0 |
| Coeff on r 14: | 0 |
| Coeff on r 16: | 0 |

The optical surface parameters of Tables 1A to 1D can be combined in many ways to provide foldable lens 100. The lens may comprise at least one toric surface on at least one side, for example the second side, so as to correct astigmatism, for example. Also, the radius of curvature, conic constant, and spherical aberration correction can be combined mathematically so as to define an optical surface of each of the first side 110 and the second side 120 of the foldable lens so as to correct monochromatic aberration, for example. The optical surface of each of the first side and the second side can be manufactured in one or more of many ways based on the mathematically defined optical surface, for example such as computer numeric control machining, diamond lath turning, molding or ablation of the lens 100 so as to provide the optical correction of the patient. Alternatively, the optical surfaces of the first side comprising the inner optical surface portion and the outer refractive surface may comprise the optical power of the foldable lens 100, and the second side of the foldable lens can be substantially flat having an optical power of about zero D.

Alternatively or in combination with the monochromatic aberration correction, the lens 100 may comprise diffractive correction on one or more of the optical surfaces, for example on the second side 120. The diffractive correction may comprise monofocal chromatic aberration correction or bifocal chromatic aberration correction, for example. The monofocal chromatic aberration correction may comprise a diffractive profile disposed on the second side 120, for example, which diffractive profile may comprise kinoform echelettes having heights corresponding to an integer number of a design wavelength of light. The bifocal chromatic aberration correction may comprise kinoform echelettes having height corresponding to a fraction of a design wavelength such as one half or three halves of the design wavelength, for example.

Figure 3:
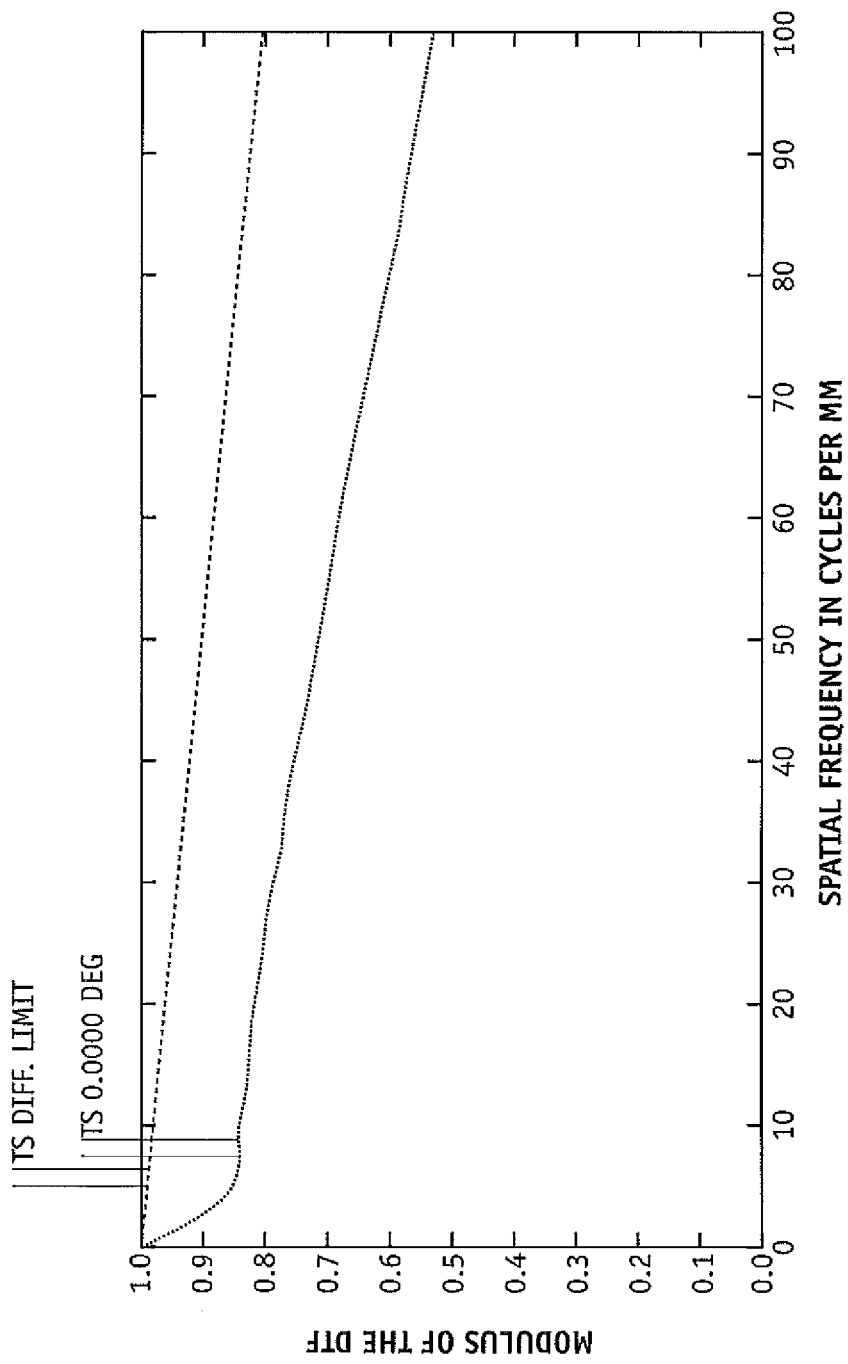
FIG. 3 shows a modulus of the optical transfer function, in accordance with embodiments of the present invention.

FIG. 3 shows a calculated modulus of the optical transfer function, in accordance with embodiments described with reference to Tables 1A to 1E and with monochromatic aberration correction comprising conic constant, fourth and sixth order spherical aberration correction for a 20 D foldable intraocular lens. The calculated modulus of the OTF is shown from a spatial frequency of 0 cycles per mm to about 100 cycles per mm on the retina based on a computer model of the eye and the cycles per mm on the retina. The modulus of the optical transfer function is about 0.7 at 50 cycles per mm, which this example corresponds to about 20/20 (6/6 metric) vision with the foldable lens 100.

While the exemplary embodiments have been described in some detail, by way of example and for clarity of understanding, those of skill in the art will recognize that a variety of modifications, adaptations and changes may be employed. Hence the scope of the present invention shall be limited solely by the claims.

What is claimed is:

1. A foldable lens for insertion into an eye of a patient through an incision, the eye having a retina, the foldable lens comprising an optically transparent foldable material having a first side disposed opposite a second side, the first side comprising an inner optical surface portion and an outer refractive surface portion disposed about the inner optical surface portion, wherein the outer refractive surface portion comprises a first plurality of convexly curved refractive profile regions comprised of a convex set radius of curvature configured to converge light energy toward a focus on the retina and a second plurality of concavely curved refractive profile regions comprised of a concave set radius of curvature configured to diverge light energy away from the focus on the retina, and wherein the foldable lens has a center, and wherein each of the first plurality of convexly curved refractive profile regions is an annular region, and each of the first plurality of convexly curved refractive profile regions is concentric to the center of the lens.

2. The foldable lens of claim 1, wherein the first plurality of convexly curved refractive profile regions comprises first annular regions and wherein the second plurality of concavely curved refractive profile regions comprises second annular regions disposed between the first annular regions.

3. The foldable lens of claim 2, wherein the second side comprises a second optical surface optically coupled to the inner optical surface portion and the outer refractive surface portion.

4. The foldable lens of claim 3, wherein the second optical surface comprises a convex refractive surface profile having a positive optical power optically coupled to the inner optical surface portion and the outer refractive surface portion and wherein each of the concavely curved refractive profile regions comprises a negative optical power stronger than the positive optical power of the convex refractive surface profile to diverge the light energy away from the focus when placed in the eye.

5. The foldable lens of claim 4, wherein each of the convexly curved refractive profile regions comprises a positive optical power coupled to the positive optical power of the convex refractive surface to direct the light energy toward the focus and wherein the negative optical power of each concavely curved refractive profile region is stronger than the positive optical power of said each of the convexly curved refractive profile regions.

6. The foldable lens of claim 4, wherein the convex refractive surface profile of the second side comprises a diffractive profile disposed thereon.

7. The foldable lens of claim 6, wherein the diffractive profile comprises one or more of a substantially monofocal diffractive profile having positive optical power to correct chromatic aberration of the eye or a multifocal diffractive profile having positive optical power to correct chromatic aberration and increase a depth of field of the focus of the eye.

8. The foldable lens of claim 4, wherein the convex refractive surface profile comprises one or more of a spherical surface, a toric surface, an aspheric surface, a conic constant, a fourth order spherical aberration correction or a sixth order spherical aberration correction to correct monochromatic aberration of the eye.

9. The foldable lens of claim 3, wherein the second optical surface comprises a diffractive surface profile having a positive optical power, the diffractive surface profile optically coupled to the inner optical surface portion and the outer refractive surface portion and wherein each of the concavely curved refractive profile region comprises a negative optical power stronger than the positive optical power of the diffractive surface profile to diverge the light energy away from the focus when placed in the eye.

10. The foldable lens of claim 1, wherein the inner optical surface portion comprises a convex refractive surface profile.

11. The foldable lens of claim 1, wherein the inner optical surface portion comprises a diffractive surface profile.

12. The foldable lens of claim 1, wherein the inner optical surface portion and the outer refractive portion of the first side comprise an aspheric surface.

13. The foldable lens of claim 3, wherein the second optical surface comprises an aspheric surface.

14. The foldable lens of claim 1, wherein the foldable lens comprises an intraocular lens having at least two haptics affixed to the lens.

15. The foldable lens of claim 1, wherein the optically transparent foldable material comprises an acrylic material.

16. The foldable lens of claim 1, wherein the lens has an optical power of at least +5 D and a center thickness of no more than about 0.7 mm.

* * * * *